United States Patent
Shields et al.

(10) Patent No.: US 9,095,347 B2
(45) Date of Patent: Aug. 4, 2015

(54) ELECTRICALLY CONDUCTIVE/INSULATIVE OVER SHOE FOR TISSUE FUSION

(75) Inventors: Chelsea Shields, Portland, OR (US); Edward C. Meagher, Greenlawn, NY (US)

(73) Assignee: Covidien AG, Neuhausen am RheinFall (CH)

( * ) Notice: Subject to any disclaimer, the term of this patent is extended or adjusted under 35 U.S.C. 154(b) by 1183 days.

(21) Appl. No.: 12/212,780

(22) Filed: Sep. 18, 2008

(65) Prior Publication Data

US 2009/0048596 A1    Feb. 19, 2009

Related U.S. Application Data

(62) Division of application No. 10/718,379, filed on Nov. 20, 2003, now Pat. No. 7,442,193.

(51) Int. Cl.
| | |
|---|---|
| *A61B 18/12* | (2006.01) |
| *A61B 18/14* | (2006.01) |
| A61B 17/00 | (2006.01) |
| A61B 18/00 | (2006.01) |

(52) U.S. Cl.
CPC ......... *A61B 18/1445* (2013.01); *A61B 18/1442* (2013.01); *A61B 2017/00296* (2013.01); *A61B 2018/0063* (2013.01); *A61B 2018/1246* (2013.01); *A61B 2018/1495* (2013.01)

(58) Field of Classification Search
CPC ........... A61B 18/1442; A61B 18/1445; A61B 2018/0063; A61B 2018/126

USPC ..................................................... 606/41–52
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |

(Continued)

FOREIGN PATENT DOCUMENTS

| | | |
|---|---|---|
| CA | 2104423 | 2/1994 |
| DE | 2415263 | 10/1975 |

(Continued)

OTHER PUBLICATIONS

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(Continued)

*Primary Examiner* — Aaron Roane

(57) ABSTRACT

An over shoe for use with electrosurgical instruments having a pair of juxtaposed jaw members pivotably associated with one another, at least one of which includes an electrically conductive surface disposed thereon which is in electrical engagement with an electrosurgical energy source. According to one aspect of the present disclosure, the over shoe includes a tissue contacting wall configured and dimensioned to selectively and substantially overlie the electrically conductive surface of the electrosurgical instrument. The tissue contacting wall is fabricated from a non-conductive material and includes a plurality of apertures formed therethrough. In another embodiment, the tissue contacting wall is electrically conductive and is configured for selective engagement atop on of the jaw members.

14 Claims, 14 Drawing Sheets

(56) References Cited

U.S. PATENT DOCUMENTS

| | | |
|---|---|---|
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,225,138 A * | 12/1940 | Traylor, Jr. ............... 222/85 |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,826,338 A * | 5/1989 | Kilpatrick ............... 401/35 |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | DeLahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | DeLahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |

(56) References Cited

U.S. PATENT DOCUMENTS

| | | |
|---|---|---|
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,512,721 A | 4/1996 | Young et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsukagoshi et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A * | 10/1997 | Fox et al. ............... 606/51 |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,895 A * | 2/1998 | Lontine et al. ............... 606/41 |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,762,435 A * | 6/1998 | Fukushima ............... 401/213 |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |

(56) References Cited

U.S. PATENT DOCUMENTS

| | | |
|---|---|---|
| 5,776,130 A | 7/1998 | Buysse et al. |
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamsom, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Dafforn et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Vandemoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |

(56) References Cited

U.S. PATENT DOCUMENTS

| | | |
|---|---|---|
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |

(56) References Cited

U.S. PATENT DOCUMENTS

| | | |
|---|---|---|
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| 7,137,980 B2 | 11/2006 | Buysse |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,298,973 B2 | 11/2007 | Ovadia |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jhigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2001/0032002 A1* | 10/2001 | McClurken et al. .......... 607/103 |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |

(56) References Cited

U.S. PATENT DOCUMENTS

| | | |
|---|---|---|
| 2005/0113826 A1 | 5/2005 | Johnson et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

FOREIGN PATENT DOCUMENTS

| | | |
|---|---|---|
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 | 4/1990 |
| EP | 0467501 | 1/1992 |
| EP | 0518230 | 12/1992 |
| EP | 0541930 | 5/1993 |
| EP | 0572131 | 12/1993 |
| EP | 0584787 | 3/1994 |
| EP | 0589453 | 3/1994 |
| EP | 0589555 | 3/1994 |
| EP | 0623316 | 11/1994 |
| EP | 0624348 | 11/1994 |
| EP | 0650701 | 5/1995 |
| EP | 0694290 | 3/1996 |
| EP | 0717966 | 6/1996 |
| EP | 0754437 | 3/1997 |
| EP | 0517243 | 9/1997 |
| EP | 0853922 | 7/1998 |
| EP | 0875209 | 11/1998 |
| EP | 0878169 | 11/1998 |
| EP | 0887046 | 1/1999 |
| EP | 0923907 | 6/1999 |
| EP | 0986990 | 3/2000 |
| EP | 1034747 | 9/2000 |
| EP | 1034748 | 9/2000 |
| EP | 1025807 | 10/2000 |
| EP | 1034746 | 10/2000 |
| EP | 1050278 | 11/2000 |
| EP | 1053719 | 11/2000 |
| EP | 1053720 | 11/2000 |
| EP | 1055399 | 11/2000 |

(56) References Cited

FOREIGN PATENT DOCUMENTS

| | | |
|---|---|---|
| EP | 1055400 | 11/2000 |
| EP | 1080694 | 3/2001 |
| EP | 1082944 | 3/2001 |
| EP | 1159926 | 12/2001 |
| EP | 1177771 | 2/2002 |
| EP | 1301135 | 4/2003 |
| EP | 1330991 | 7/2003 |
| EP | 1486177 | 6/2004 |
| EP | 1472984 | 11/2004 |
| EP | 0774232 | 1/2005 |
| EP | 1527747 | 5/2005 |
| EP | 1530952 | 5/2005 |
| EP | 1532932 | 5/2005 |
| EP | 1535581 | 6/2005 |
| EP | 1609430 | 12/2005 |
| EP | 1632192 | 3/2006 |
| EP | 1642543 | 4/2006 |
| EP | 1645238 | 4/2006 |
| EP | 1645240 | 4/2006 |
| EP | 1649821 | 4/2006 |
| EP | 1707143 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000-342599 A2 | 12/2000 |
| JP | 2000-350732 A2 | 12/2000 |
| JP | 2001-008944 A2 | 1/2001 |
| JP | 2001-029356 A2 | 2/2001 |
| JP | 2001-128990 A2 | 5/2001 |
| RU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.

(56) References Cited

OTHER PUBLICATIONS

Muller et al., "Extended Left Hemicolectomy Using the LigaSure Vessel Sealing System" Innovations That Work, Sep. 1999.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Herman et al., "Laparoscopic Intestinal Resection With the LigaSure Vessel Sealing System: A Case Report"; Innovations That Work, Feb. 2002.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Paul G. Horgan, "A Novel Technique for Parenchymal Division During Hepatectomy" The American Journal of Surgery, vol. 181, No. 3, Apr. 2001 pp. 236-237.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Craig Johnson, "Use of the LigaSure Bessel Sealing System in Bloodless Hemorrhoidectomy" Innovations That Work, Mar. 2000.
Int'l Search Report EP 98944778 dated Oct. 31, 2000.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.

\* cited by examiner

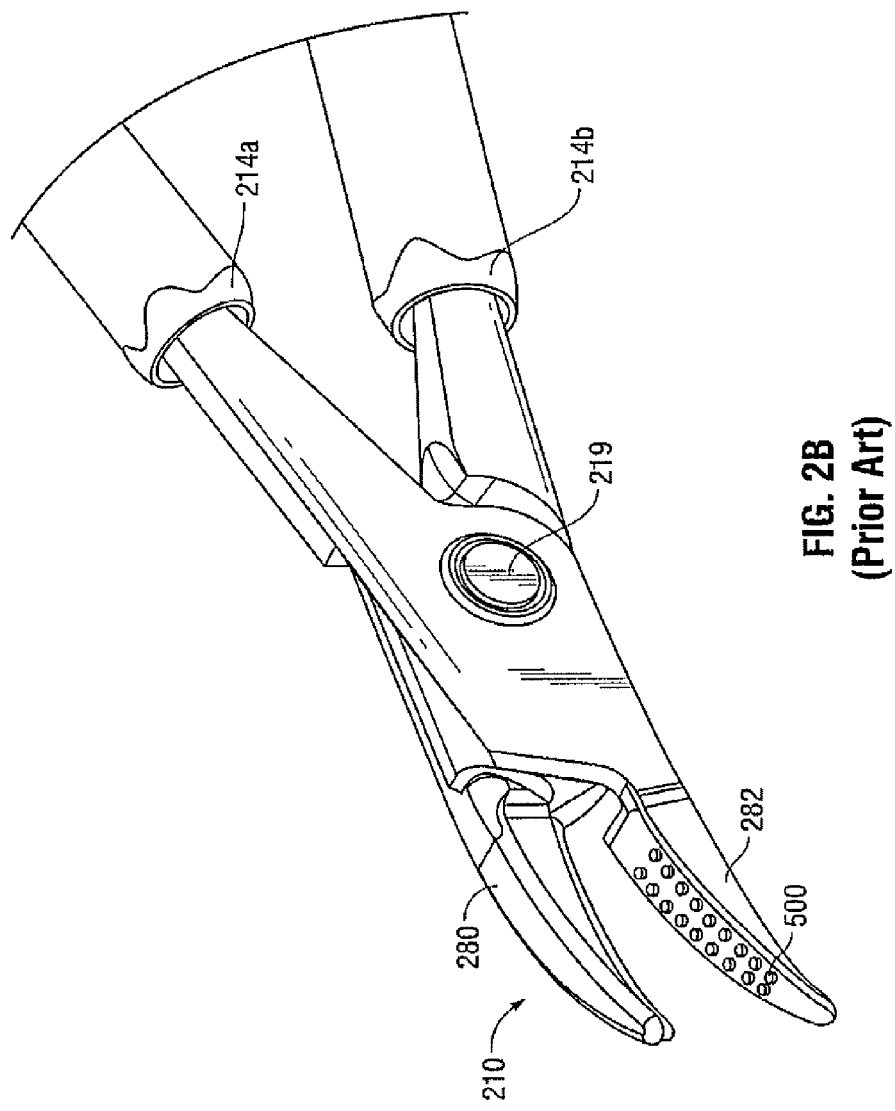

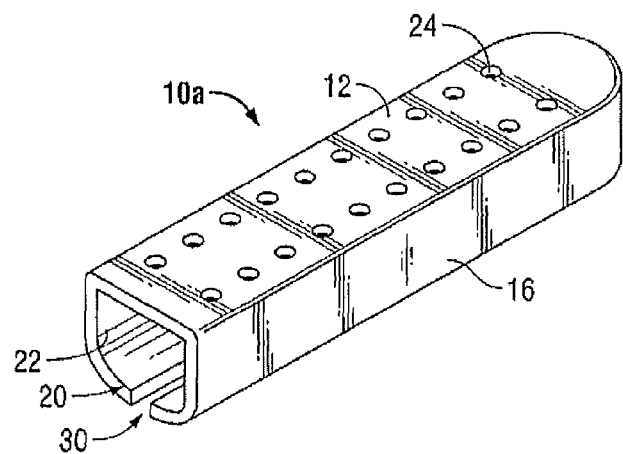
FIG. 5
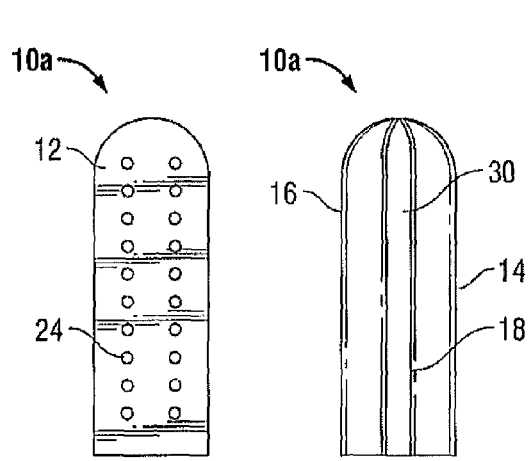
FIG. 6    FIG. 7
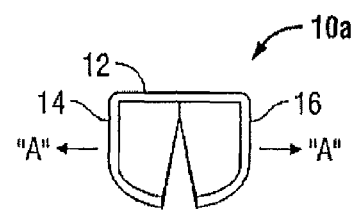
FIG. 8
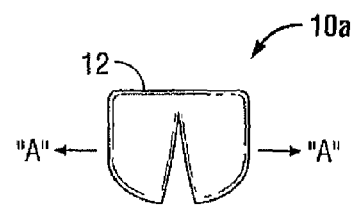
FIG. 9

ELECTRICALLY CONDUCTIVE/INSULATIVE OVER SHOE FOR TISSUE FUSION

CROSS-REFERENCE TO RELATED APPLICATION

The present application is a Divisional Application claiming the benefit of and priority to U.S. application Ser. No. 10/718,379, now U.S. Pat. No. 7,442,193, filed on Nov. 20, 2003, the entire content of which is incorporated herein by reference.

BACKGROUND

1. Technical Field

The present disclosure relates to electrosurgical instruments and, more particularly, an over-shoe for use in cooperation with electrosurgical instruments for controlling the amount of electrosurgical energy delivered to the tissue.

2. Description of Related Art

A hemostat and/or forceps is a simple plier-like tool which uses mechanical action between its jaws to constrict vessels and is commonly used in open surgical procedures to grasp, dissect and/or clamp tissue. Electrosurgical hemostats and/or forceps utilize both mechanical clamping action and electrical energy to effect hemostasis by heating the tissue and blood vessels, between its jaws, to cut, blend and/or coagulate tissue. An electrode operatively associated with each opposing jaw member is charged to a different electric potential such that when the jaw members grasp tissue therebetween, electrical energy can be selectively transferred through the tissue. A surgeon can cut, blend, coagulate/desiccate and/or simply reduce or slow bleeding, by controlling the intensity, frequency and duration of the electrosurgical energy applied between the electrodes and through the tissue.

"Tissue heating" is generally proportional to the square of the amount of current being generated through tissue while "tissue vaporization" is generally proportional to current and is generally proportional to the amount of energy in an arc. The amount of energy in the arc, in combination with the "Cathode Fall Voltage", derives the "power for vaporization". "Thermal spread" is dependent on the amount of heat generated within the tissue and is dependent on tissue resistivity and the arc energy squared. As can be appreciated, the control of "thermal spread" is an important factor in determining and controlling the depth of tissue treatment.

Accordingly, during electrosurgery, an increase or decrease in the amount of current provides and/or creates a different effect on the tissue. This phenomenon is due to a variable referred to as the crest factor (CF). The crest factor can be calculated using the formula: $CF=V_{PEAK_1}/V_{RMS}$, where $V_{PEAK}$ is the positive peak of the waveform and $V_{RMS}$ is the "Root Mean Square" or RMS value of the waveform. The crest factor can also be calculated using the formula: $CF=[(1-D)/D]^{1/2}$, where D is the duty cycle of the waveform and is defined as $D=T_1/(T_1+T_2)$.

An increase in the crest factor results in more current per arc at a given power setting. Further, "since tissue heating" is proportional to the current through the tissue squared, and "tissue vaporization" is proportional to the amount of current being generated through the tissue, a doubling of current per arc results in four times as much tissue heating and twice the amount of tissue vaporization when an electrode of an electrosurgical hemostat and/or forceps, connected to the electrosurgical generator system, contacts the tissue.

Based on the above formulas, it is evident that when operating an electrosurgical generator system in either the "cut", "blend", "coagulate" or seal mode, the range of the crest factor varies from one mode to another. For the purposes herein, "coagulation" is defined as a process of desiccating tissue wherein the tissue cells are ruptured and dried. "Vessel sealing" is defined as the process of liquefying the collagen in the tissue so that it reforms into a fused mass with significantly-reduced demarcation between the opposing tissue structures (opposing walls of the lumen). Coagulation of small vessels is usually sufficient to permanently close them. Larger vessels need to be sealed to assure permanent closure.

Commonly assigned U.S. Application Serial Nos. PCT Application Serial No. PCT/US01/11340; U.S. application Ser. No. 10/116,824; and PCT Application Serial No. PCT/US01/11420 (all of which are hereby incorporated by reference herein) teach that to effectively seal tissue or vessels, especially large vessels, two predominant mechanical parameters must be accurately controlled: 1) the pressure applied to the vessel; and 2) the gap distance between the conductive tissue contacting surfaces (electrodes). As can be appreciated, both of these parameters are affected by the thickness of the vessel or tissue being sealed. Accurate application of pressure is important for several reasons: 1) to oppose the walls of the vessel; 2) to reduce the tissue impedance to a low enough value that allows enough electrosurgical energy through the tissue; 3) to overcome the forces of expansion during tissue heating; and 4) to contribute to the end tissue thickness which is an indication of a good seal. It has been determined that a typical sealed vessel wall is optimum between about 0.001 inches and about 0.006 inches.

With respect to electrosurgically treating relatively smaller vessels, for effective sealing, the pressure applied to the vessel becomes less relevant and the gap distance between the electrically conductive surfaces of the electrodes becomes more significant. In other words, the chances of the two electrodes touching one another during activation increases as the tissue thickness and the vessels become smaller.

As can be appreciated, when cutting, blending or coagulating vessels, the tissue disposed between the two opposing jaw members is essentially destroyed. Other known electrosurgical instruments include blade members or shearing members which simply cut tissue in a mechanical and/or electromechanical manner and, as such, also destroy tissue viability. With respect to electrosurgically treating relatively larger vessels and/or soft tissues (e.g., lung, intestine, lymph ducts, etc.), to promote healing, the above-identified surgical treatments are generally impractical due to the fact that in each instance the tissue or a significant portion thereof is essentially destroyed to create the desired surgical effect (e.g., cutting, blending and/or cauterizing) which does not promote healing.

Accordingly, the need exists for electrosurgical accessories and/or devices (e.g., an electrically conductive or insulative over shoe) which can be used in cooperation with existing electrosurgical instruments (e.g., electrosurgical forceps) for controlling and/or limiting the current (or current per arc on a micro level) and for controlling the degree of tissue heating and the degree of tissue vaporization.

In addition, the need exists for electrosurgical accessories and/or devices (e.g., an electrically conductive or insulative over shoe) for cooperative use with existing electrosurgical instruments (e.g., electrosurgical forceps) which allow for the effective treatment of tissue and the effective maintenance of tissue viability across the treatment area to promote tissue healing.

SUMMARY

The present disclosure relates to an over shoe for use with electrosurgical instruments having a pair of juxtaposed jaw members pivotably associated with one another. At least one of the jaw members includes an electrically conductive surface disposed thereon and in electrical engagement with an electrosurgical energy source is disclosed. According to one aspect of the present disclosure, the over shoe includes a tissue contacting wall configured and dimensioned to selectively and substantially overlie (or be selectively positioned atop) the electrically conductive surface of the electrosurgical instrument. The tissue contacting wall is preferably fabricated from a non-conductive material and includes a plurality of apertures formed therethrough.

In one embodiment the over shoe includes a tissue contacting wall fabricated from a ceramic material. The tissue contacting wall desirably includes a plurality of apertures arranged in pairs along a length of the electrically conductive surface. It is envisioned that the apertures are randomly arranged.

It is contemplated that the apertures are evenly sized. It is further envisioned that the apertures are generally circular. In one embodiment, the apertures can have diameters of about 0.000394 inches (10 µm) to about 0.0394 inches (1000 µm). In another embodiment, the apertures may be much larger and being the range of about 0.001 inches (0.0254 millimeters) to about 0.15 inches (3.81 millimeters).

It is further contemplated that the apertures are elongated slots. The elongated slots can be in at least one of a parallel orientation with respect to the longitudinal axis and at an angle with respect to the longitudinal axis.

It is envisioned that the over shoe can further include a pair of side walls extending from lateral side edges of the tissue contacting wall, and a bottom wall interconnecting the pair of side walls, the tissue contacting wall, the bottom wall and the side walls defining a cavity configured and dimensioned to substantially receive a jaw member of the electrosurgical instrument. The bottom wall can include a longitudinally oriented slot running along a length thereof which promotes friction fit engagement between the over shoe and the jaw member.

The over shoe can include at least one band extending between and engaged with each side terminal edge of the tissue contacting wall. The over shoe can include at least one inter-engaging member extending from an inner surface of at least one of the pair of side walls, the at least one inter-engaging member being configured and dimensioned to engage a complementary recess formed in the jaw member. The at least one inter-engaging member registers the apertures of an over shoe placed on one of the pair of jaw members relative to the apertures of an over shoe placed on the other of the other of the pair of jaw members. It is contemplated that the apertures can be in vertical registration and/or offset.

The tissue contacting wall can have a thickness which is in the range of about 0.000394 inches (10 µm) to about 0.0394 inches (1000 µm). The thickness of the tissue contacting wall is non-uniform.

According to another aspect of the present disclosure, the over shoe can include a tissue contacting wall fabricated from a non-conductive material, the tissue contacting wall being configured and dimensioned to over lie an electrically conductive surface disposed on the electrosurgical instrument, the tissue contacting wall including at least one aperture extending therethrough. The tissue contacting wall is desirably fabricated from a ceramic material.

It is envisioned that the tissue contacting wall is fabricated from materials having a high Comparative Tracking Index, preferably the range of about 300 to about 600 volts.

It is further envisioned that the tissue contacting wall is fabricated from a group consisting of at least one of nylons, syndiotactic polystryrenes, polybutylene terephthalate, polycarbonate, acrylonitrile butadiene styrene, polyphthalamide, polymide, polyethylene terephthalate, polyamide-imide, acrylic, polystyrene, polyether sulfone, aliphatic polyketone, acetal copolymer, polyurethane, nylon with polyphenyleneoxide dispersion, and acrylonitrile styrene acrylate.

The present disclosure also relates to an over shoe for use with electrosurgical instruments which is capable of performing tissue sealing between two opposing jaw members, the over shoe including a tissue contacting wall fabricated from a conductive material which is disposed in electrical communication with a source of electrosurgical energy. The tissue contacting wall also includes at least one sidewall which depends therefrom which defines a slot for selectively receiving at least one jaw member. The tissue contacting wall also includes at least one aperture which extends therethrough. Preferably, the jaw member is made from an insulative material.

A second over shoe may be included which is designed to substantially overlie or sit atop the second jaw member such that the jaw members are capable of conducting bipolar energy therethrough.

The present disclosure also relates to an over shoe for use with electrosurgical instruments capable of performing tissue sealing between two opposing jaw members which includes a tissue contacting wall fabricated from a non-conductive material. The tissue contacting wall includes at least one sidewall which depends therefrom which defines a slot for selectively receiving at least one jaw member. The tissue contacting wall also includes at least one protrusion extending therefrom, the protrusion being disposed in electrical communication with a source of electrosurgical energy. For bipolar electrosurgical instruments, each jaw member may include an electrically conductive over shoe.

Further features of the above embodiments will become more readily apparent to those skilled in the art from the following detailed description of the apparatus taken in conjunction with the drawings.

BRIEF DESCRIPTION OF THE DRAWINGS

Various embodiments will be described herein below with reference to the drawings, wherein:

FIG. 2B is an enlarged perspective view of a jaw assembly of the prior art open forceps of FIG. 2A;

FIG. 5 is a rear perspective view of an over shoe in accordance with yet another embodiment of the present disclosure;

FIG. 6 is a top plan view of the over shoe of FIG. 5;

FIG. 7 is a bottom plan view of the over shoe of FIGS. 5 and 6;

FIG. 8 is a rear elevational view of the over shoe of FIGS. 5-7;

FIG. 9 is a front elevational view of the over shoe of FIGS. 5-8;

DETAILED DESCRIPTION

Figure 1A:
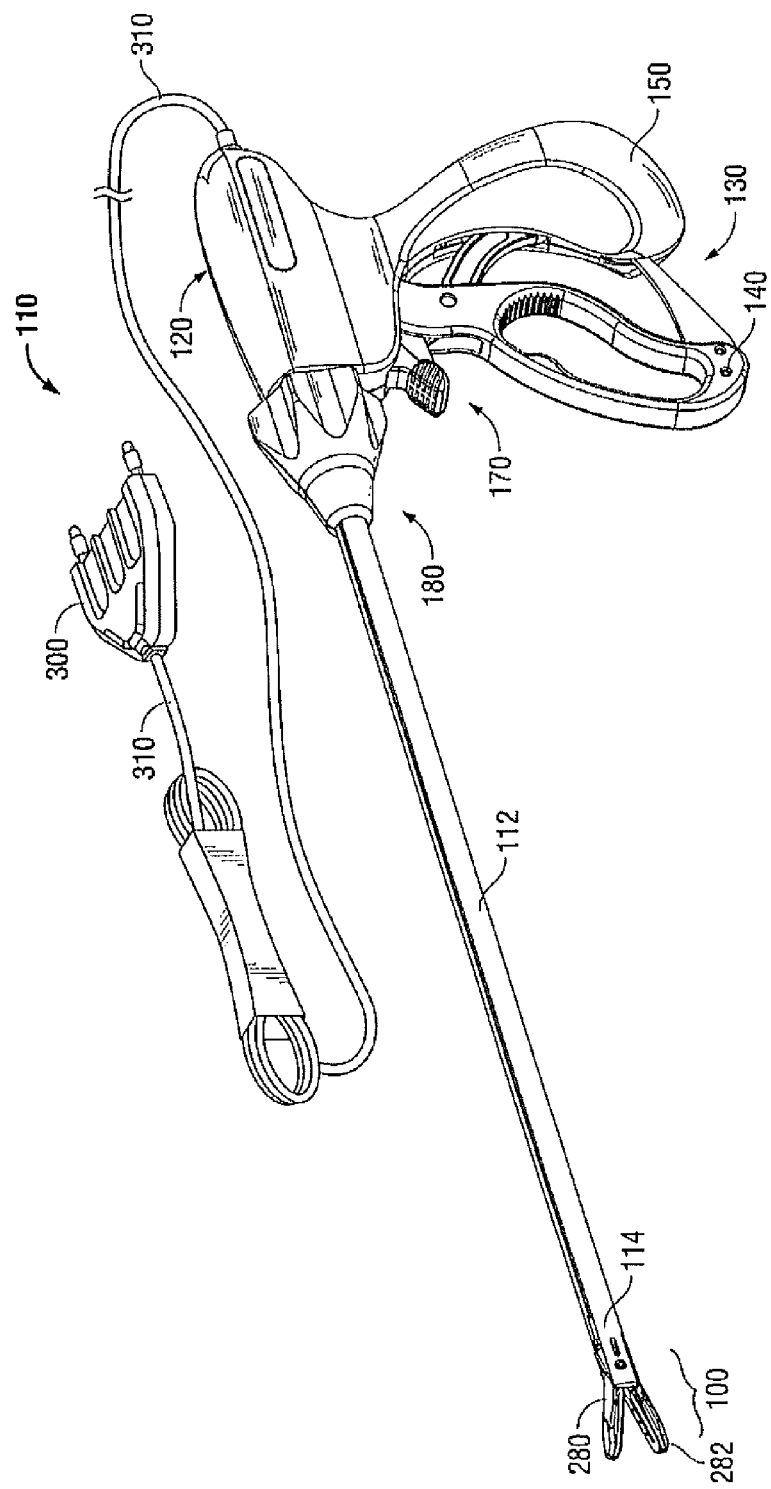
FIG. 1A is a perspective view of a prior art endoscopic forceps.

Preferred embodiments of the presently disclosed instruments, devices and accessories will now be described in detail with reference to the drawing figures wherein like reference numerals identify similar or identical elements. In the drawings and in the description which follows, the term "proximal", as is traditional, will refer to the end of the instrument, device and/or accessory which is closest to the operator while the term "distal" will refer to the end of the instrument, device and/or accessory which is furthest from the operator.

Figure 1B:
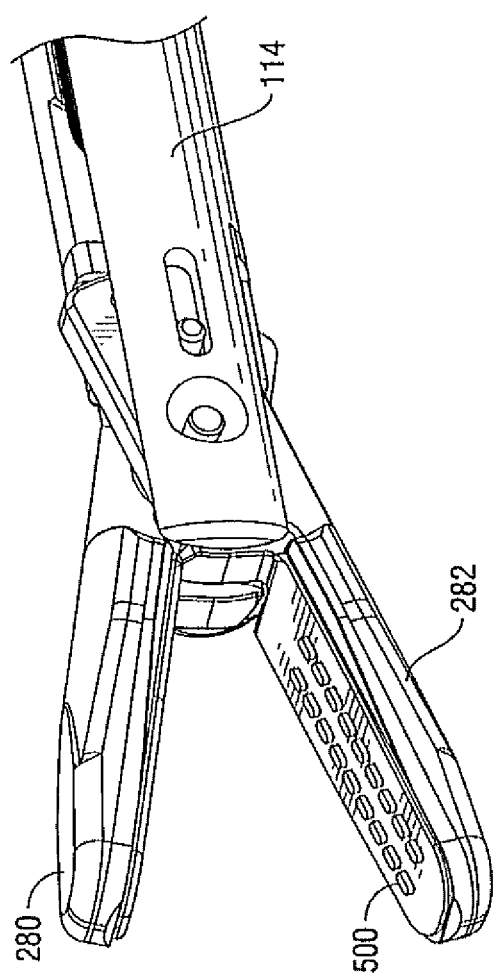
FIG. 1B is an enlarged perspective view of a jaw assembly of the prior art endoscopic forceps of FIG. 1A.

Referring to FIGS. 1A and 1B, a prior art bipolar forceps, for use in various endoscopic surgical procedures, is shown generally as 100. Forceps 100 generally includes a housing 120, a handle assembly 130, a rotating assembly 180, an activation assembly 170 and an electrode assembly 110 which mutually cooperate to grasp and seal tissue.

More particularly, forceps 100 includes a shaft 112 which has a distal end 114 dimensioned to mechanically engage a jaw assembly 110 and a proximal end 116 which mechanically engages housing 120. Shaft 112 may be bifurcated at the distal end 114 thereof to receive jaw assembly 110. Proximal end 116 of shaft 112 mechanically engages rotating assembly 180 to facilitate rotation of jaw assembly 110.

Forceps 100 also includes an electrical interface or plug 300 which connects forceps 100 to a source of electrosurgical energy, e.g., an electrosurgical generator (not shown). An electrical cable 310 extends from plug 300 and is securely connected to housing 120 of forceps 100. Cable 310 is internally divided within housing 120 to transmit electrosurgical energy through various electrical feed paths to jaw assembly 110. Handle assembly 130 includes a fixed handle 150 and a movable handle 140. Fixed handle 150 is integrally associated with housing 120 and handle 140 is movable relative to fixed handle 150 to actuate a pair of opposing jaw members 280 and 282 of jaw assembly 110.

Figure 2A:
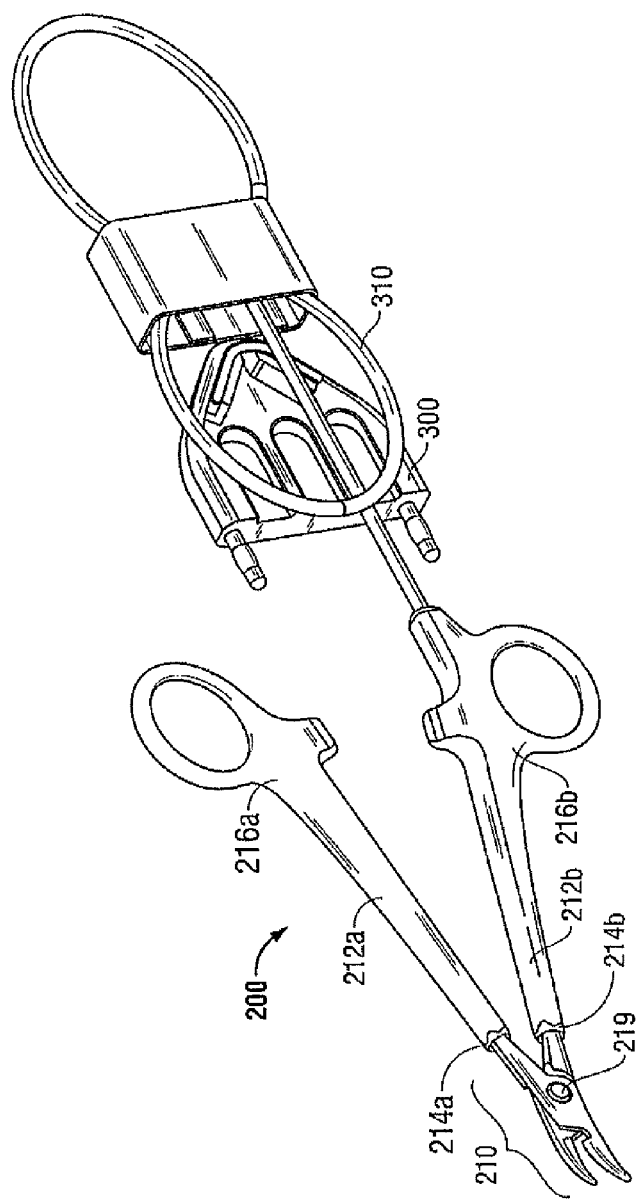
FIG. 2A is a perspective view of a prior art open forceps.

Referring now to FIGS. 2A and 2B, a prior art open forceps is generally shown as 200. Open forceps 200 is generally in the form of a pair of scissors and includes a pair of elongated shaft portions 212a, 212b each having a proximal end 216a, 216b, respectively, and a distal end 214a, 214b, respectively. Open forceps 200 includes a jaw assembly 210 which attaches to distal end 214a, 214b of shaft portions 212a, 212b, respectively. Jaw assembly 210 includes opposing jaw members 280, 282 which are pivotably connected about a pivot pin 219.

One of shafts 212a, 212b, is operatively connected to a source of electrosurgical energy, such as an electrosurgical generator (not shown), via an electrosurgical cable 310. A proximal end of cable 310 includes a similar plug 300 as described above.

As best seen in FIGS. 1B and 2B, various electrical connections of electrode assemblies 110, 210 (not shown) are configured to provide electrical continuity to an array of electrode micro-sealing pads 500 disposed along one or both jaw members 280, 282. Commonly-assigned U.S. patent application Ser. No. 10/369,894 shows one example of an open forceps having a plurality of micro sealing pads 500 disposed on opposing electrically conductive surfaces for maintaining the viability of tissue after sealing. The contents of U.S. patent Ser. No. 10/369,894 are hereby incorporated by reference herein.

As disclosed, electrode micro-sealing pads 500 are arranged in a longitudinal, pair-like fashion along the tissue contacting surfaces of jaw members 280, 282. In use, the arrangement of micro-sealing pads 500, across the tissue, only seals the tissue which is between each micro-sealing pad 500 and the opposing jaw members 280, 282. The tissue adjacent each micro-sealing pad 500 remains viable which, as can be appreciated, allows blood and nutrients to flow through the sealed tissue and between the individual tissue welds to promote tissue healing and reduce the possibility of tissue necrosis.

Figure 3:
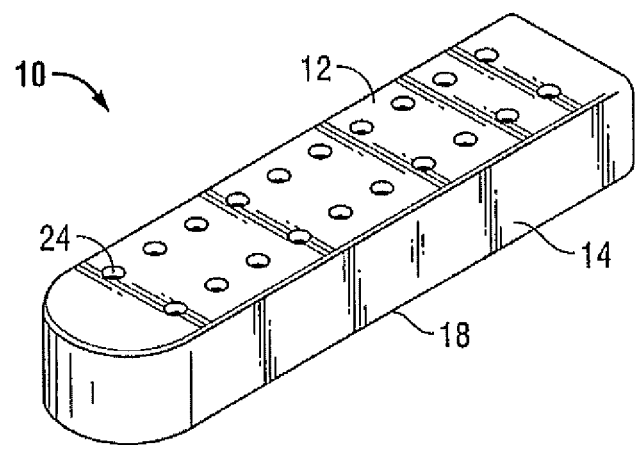
FIG. 3 is a front perspective view of an over shoe in accordance with an embodiment of the present disclosure.
Figure 4:
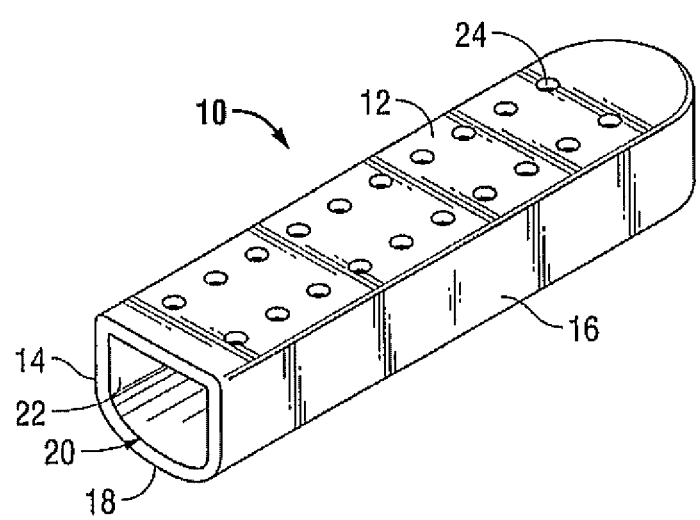
FIG. 4 is a rear perspective view of the over shoe of FIG. 3.

Turning now to FIGS. 3 and 4, an over shoe for operative engagement with at least one of the pair of opposing jaw members 280, 282 of jaw assembly 110 of forceps 100 is shown generally as 10. For the purposes herein, over shoe 10 can be used with either an endoscopic forceps (as depicted in FIGS. 1A and 1B) or an open forceps (as depicted in FIGS. 2A and 2B). Obviously, different geometric considerations apply to use over shoe 10 with each particular type of instrument, however, the novel aspects with respect to over shoe 10 and its operating characteristics remain generally consistent with respect to both open and/or endoscopic forceps.

Over shoe 10 includes a tissue contacting wall 12 and a pair of side walls 14, 16 terminating in an arcuate bottom wall 18. Walls 12-18 of over shoe 10 define a cavity 20 therein sized and dimensioned to receive one of the pair of opposing jaw members 280, 282 therein. Over shoe 10 includes an opening 22 at a proximal end thereof for insertion of one of the pair of opposing jaw members 280, 282 therethrough (i.e., such that over shoe 10 can be "slipped" on over at least one of the pair of opposing jaw members 280, 282).

Over shoe 10 preferably includes a plurality of apertures 24 formed in tissue contacting wall 12 thereof. Preferably, apertures 24, as seen in FIGS. 3 and 4, are arranged in two linear rows, however, any arrangement and/or configuration of apertures 24 is envisioned and contemplated (see FIGS. 12-15), e.g., longitudinally offset rows.

In one embodiment, at least the upper, tissue engaging surface 12 of over shoe 10 is fabricated from a non-conductive material which acts to electrically (and/or thermally) insulate the majority of the tissue engaging wall 12 during activation allowing only a portion of electrosurgical energy through apertures 24. Alternatively and as described in more detail herein, it is also envisioned that the tissue engaging surface 12 may be electrically conductive (and/or thermally conductive or thermally non-conductive) and the apertures 24 non-conductive (and/or the end effector under the over shoe 10 is non-conductive).

Moreover, it is also contemplate that the apertures may vary greatly in size depending upon a particular purpose. For example and as mentioned above, the apertures 24 may be configured in many geometric configurations atop tissue contacting surface 12 which, depending upon the positioning of the apertures and whether the surface 12 is electrically conductive, electrically insulative and/or thermally insulative, will vary the desired tissue effect, e.g., cut, coagulate, blend, seal. In addition to the various geometric parameters which can greatly effect the tissue effect, it is envisioned that the size of the apertures 24 can also play an important role in determining tissue effect. For example, the apertures 24 may be relatively large (from arrange of about 0.001 inches in diameter to about 0.15 inches in diameter (or larger)) for sealing large tissues to maintain viability across the tissue seal as described in commonly owned, U.S. application Ser. No. 10/369,894 the entire contents of which are hereby incorporated by reference herein.

The apertures 24 may also be very small apertures 24 (a diameter in the range of about 0.000394 inches (10 μm) to about 0.0394 inches (1000 μm)) for limiting the current per arc through the tissue surface 12 for creating certain surgical effects as described in commonly-owned, Provisional Application No. 60/432,385 (now U.S. patent application Ser. No. [2879 (203-3439] the entire contents of which are hereby incorporated by reference herein. When the tissue engaging surface 12 is fabricated from non-conductive material, the non-conductive material essentially "pinches" or splits the arc current generated by the electrosurgical generator into a small diameter channel, effectively keeping the same current and voltage, but creating several small arcs from one large arc. Essentially, this has the effect of separating the arc current, effectively increasing the current effect to the tissue, resulting in a finer cut and/or other surgical effect. In other words, the non-conductive material enables a low frequency current to achieve surgical effects and/or results indicative of a high frequency current, while minimizing or preventing thermal damage to adjacent tissue.

As mentioned above, apertures 24 may have a uniform diameter in the range of about 0.000394 inches (10 μm) to about 0.0394 inches (1000 μm). The number of small arcs created from one large arc is inversely proportional to the diameter of apertures 24 formed in tissue contacting wall 12. Preferably, the diameter of each aperture 24 is less than the diameter of the large arc. Hence, when electrosurgical current is applied, for example, to electrode assembly 110 of forceps 100, when over shoe 10 is placed thereon, the arc current is split between apertures 24, thereby controlling or limiting the arc current through each aperture 24. This effect which controls or limits the arc current through each aperture 24 is referred to as "MicroHollow Cathode Discharge" (MCD or MHCD). Commonly owned International Patent Application Serial No. PCT/US03/08146, discloses a porous coating which may be utilized to control arc current, the entire contents being hereby incorporated by reference herein. A large arc area is desired when operating the electrosurgical generator in the coagulation mode while a small arc area is desired when operating the electrosurgical generator in the cut mode.

Moreover, it is envisioned that a series of different over shoes 10 may be sold as a pack to change the desired surgical effect based on size of apertures, geometrical configuration or layout of the apertures for cut, coagulation, sealing, blend, etc.)

In one embodiment, over shoe 10 is made from an insulative material such as ceramic due to its hardness and inherent ability to withstand high temperature fluctuations. Alternatively, over shoe 10 may be made from a material or a combination of materials having a high Comparative Tracking Index (CTI) in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

Figure 18A:
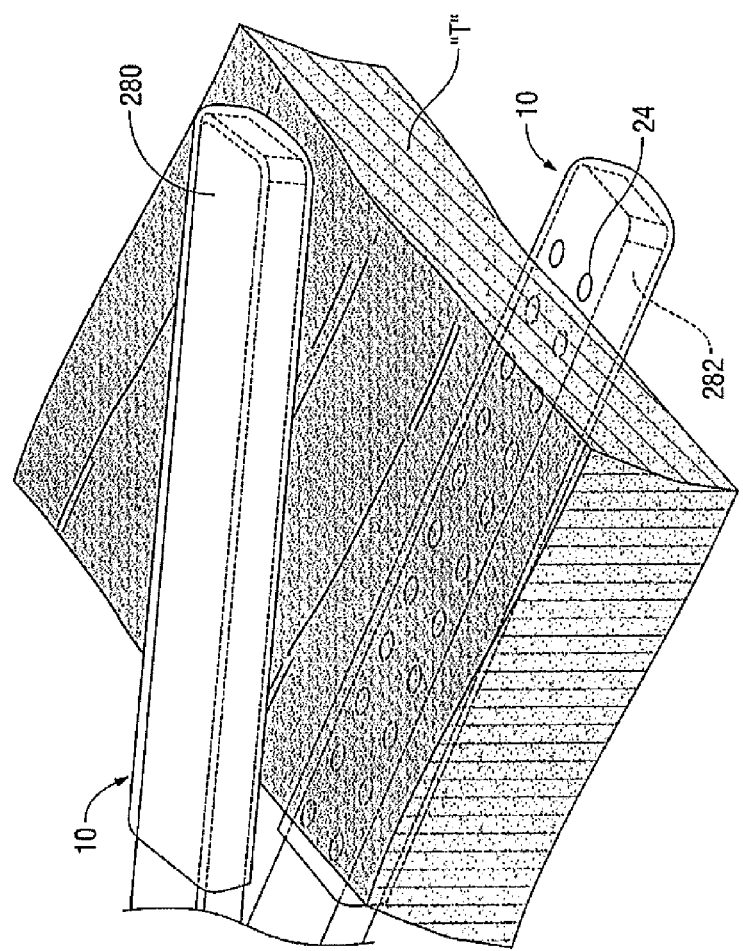
FIG. 18A is a schematic, perspective view of exemplary jaw members approximating tissue including an over shoe, in accordance with the present disclosure, placed on at least one of the jaw members.
Figure 18B:
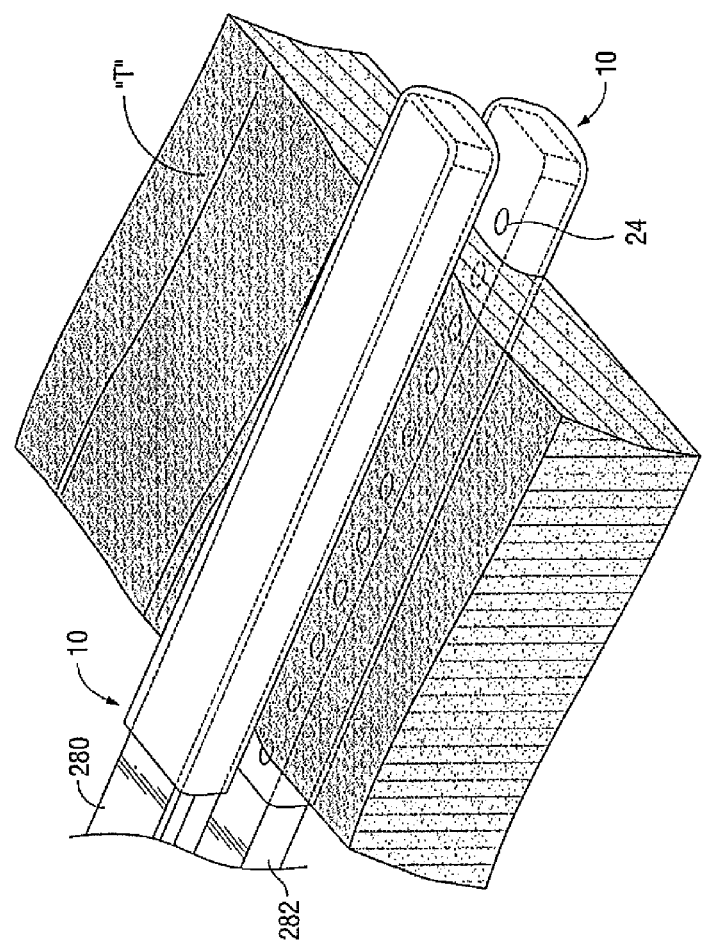
FIG. 18B is a schematic, perspective view of exemplary jaw members grasping tissue including an over shoe, in accordance with the present disclosure, placed on at least one of the jaw members.
Figure 18C:
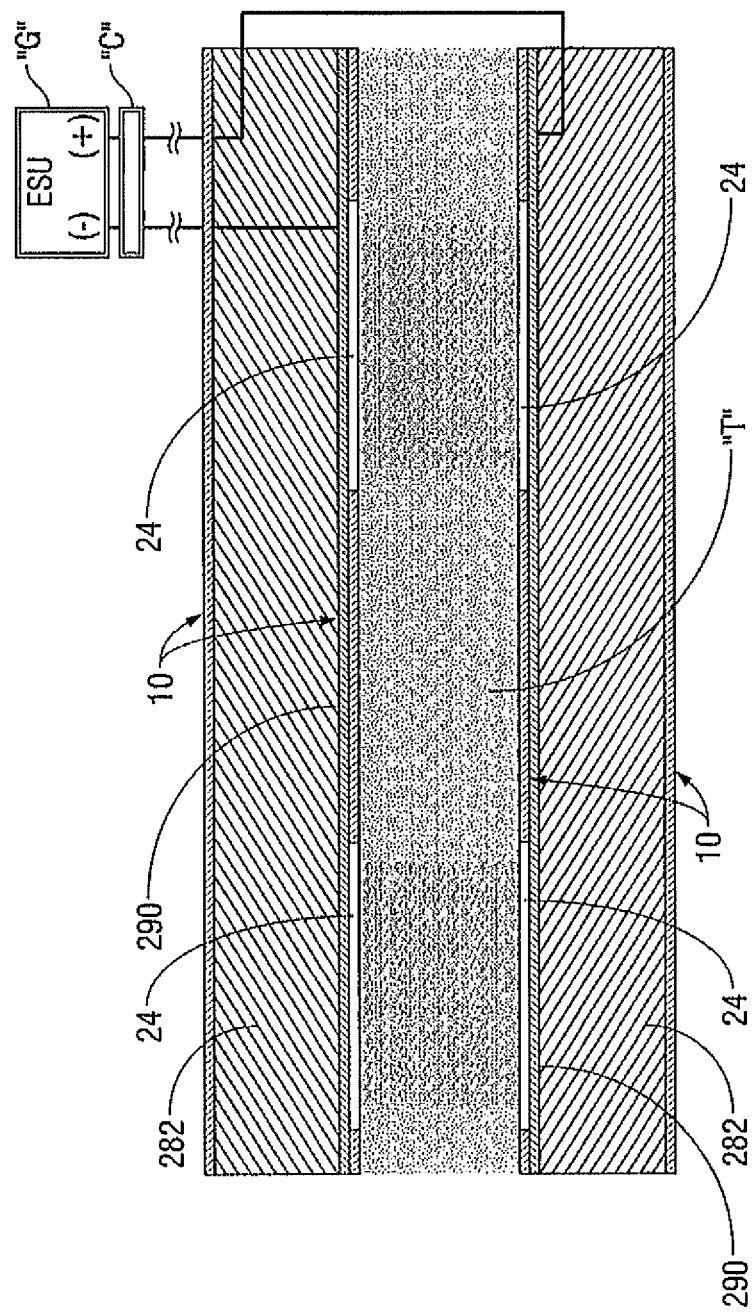
FIG. 18C is an enlarged schematic side elevational view showing the individual micro-seal sites and the viable tissue areas between the two jaw members after activation of the electrode assembly.
Figure 18D:
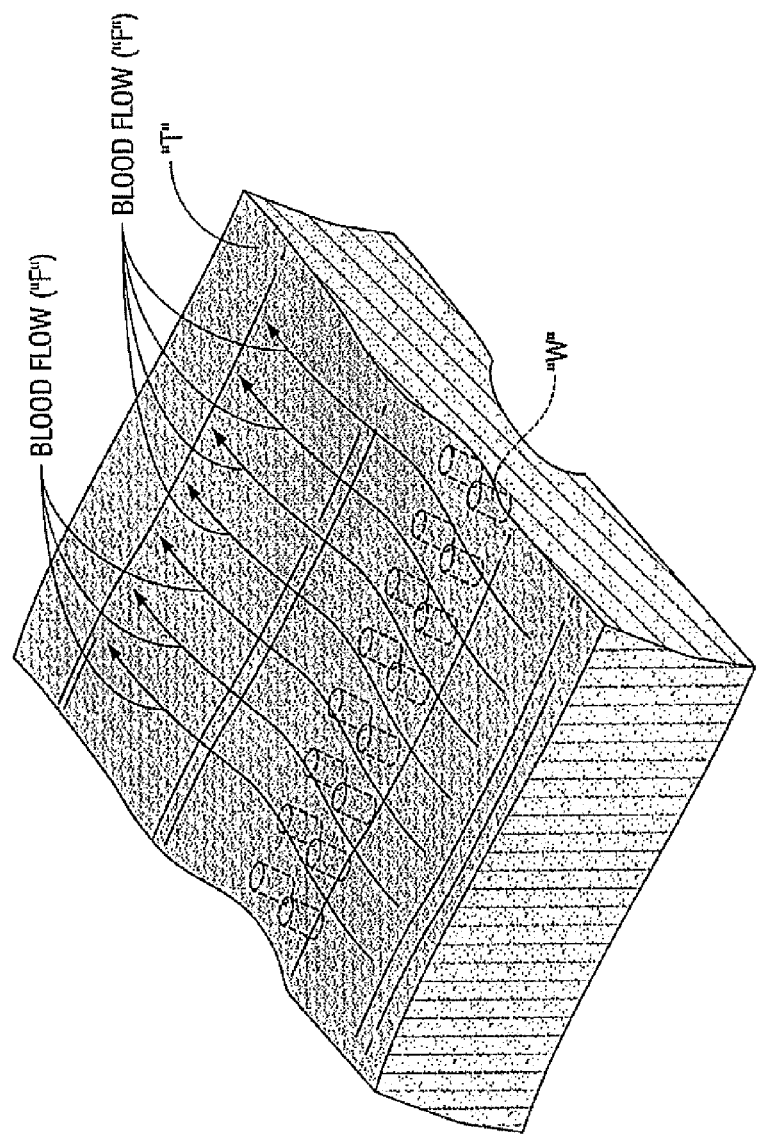
FIG. 18D is a schematic, perspective view showing a series of micro-seals disposed in a pattern across the tissue after activation of the electrode assembly.

The diameter of each of the plurality of apertures 24 can vary in size to produce different surgical effects when operating the electrosurgical generator system in one of several modes, such as, for example, in seal, cut, blend and coagulation modes. In any of these embodiments, the size of the aperture enables the surgeon to control the proportion of tissue vaporization to tissue heating, in order to achieve more controllable and desirable surgical effects. For example, relatively larger apertures 24 (e.g., on the order of about 0.001 inches to about 0.15 inches in diameter (or larger)) are desirable for effecting sealing of relatively large tissue in order to create a micro-sealing pattern across the tissue (see FIG. 18D). Moreover, relatively smaller apertures 24 are desirable for effecting cutting, blending and/or coagulating of relatively smaller tissue. It is envisioned and within the scope of the present disclosure that tissue contacting wall 12 of over shoe 10 can include regions wherein at least one of the regions includes apertures 24 sized to provide one tissue effect, e.g., sealing, and at least one other region includes apertures 24 sized to provide a different surgical effect, e.g., cutting, blending and/or coagulating.

The number of apertures 24 per square centimeter can be uniform or vary along the length of over shoe 10 and/or electrode assembly 110 of forceps 100. The number of apertures 24 per square inch (or per square centimeter) controls the overall treatment area or on a micro scale the arc area. For example, as the number of apertures 24 per square inch (or per square centimeter) increases, the treatment area decreases, and vice-versa. When the tissue surface 12 is electrically conductive, the opposite is true.

Tissue contacting wall 12 of over shoe 10 has a thickness which in turn defines the thickness and/or depth of apertures 24. For a system wherein the apertures are on a micro scale, the thickness of tissue contacting wall 12 controls the system resistance and voltage needed to establish the arc. The thicker tissue contacting wall 12 the greater the system resistance and voltage needed to establish the arc, and vice-versa.

Preferably, tissue contacting wall 12 has a thickness which is predetermined during fabrication of over shoe 10 for effectively operating electrode assembly 110 of forceps 100 in one of several modes, such as seal cut, coagulate and blend, by using the electrosurgical generator. For example, it is envisioned that the tissue contacting wall 12 may have a relatively small thickness, in the range of about 10 μm to about 500 μm, is preferred for operating electrode assembly 110 of forceps 100 in a "cut" mode; tissue contacting wall 12 having a relatively medium thickness, in the range of about 250 μm to about 1 mm, is preferred for operating electrode assembly 110 of forceps 100 in a "blend" mode; and tissue contacting wall 12 having a relatively large thickness, in the range of about 500 μm to 2 mm, is preferred for operating electrode assembly 110 of forceps 100 in the "coagulate" mode.

It is envisioned that the thickness of tissue contacting wall 12 can be varied along the length and/or the width thereof in order to be able to effectively operate electrode assembly 110 of forceps 100 in more than one mode by using the electrosurgical generator at one fixed setting. For example, tissue contacting wall 12 can have a first portion having a first thickness for operating electrode assembly 110 of forceps 100 in one of the seal, cut, blend and coagulate modes and at least one second portion having a second thickness for operating electrode assembly 110 of forceps 100 in another of the seal, cut, blend and coagulate modes.

In one method of use, an over shoe 10 can be placed over each jaw member 280, 282 of forceps 100 or 200, which over shoes 10 are dimensioned in such a manner that may simultaneously effect coagulation between portions of jaw members 280, 282 and effect tissue cutting between other portions of jaw members 280, 282. More particularly, in the areas where tissue contacting walls 12 of over shoes 10 is thicker the tissue held between jaw members 280, 282 will tend to coagulate and in the areas where tissue contacting walls 12 of over shoes 10 is thinner the tissue held between jaw members 280, 282 will tend to be cut. Accordingly, as can be appreciated, a single energy activation of the electrosurgical generator may yield a dual tissue effect which greatly simplifies the coagulating and dividing of tissue.

Similarly, an over shoe may be dimensioned to seal and cut tissue by controlling the thickness of the over shoe along the length or width of each jaw member 280, 282. As can be appreciated, by utilizing a combination of controlling gap distance and sealing pressure and controlling the current to the tissue, a surgeon may simultaneously seal and cut tissue disposed between jaw members 280, 282 due to the unique configuration of the over shoe.

While the insulating type over shoe 10 has been described as being manufactured entirely of a ceramic material, it is envisioned and within the scope of the present disclosure that only tissue contacting wall 12 needs to be manufactured from a ceramic material while the remainder of over shoe 10 (e.g., side walls 14, 16 and bottom wall 18) can be manufactured from some other rigid and/or flexible non-conductive material, such as, for example, plastic, latex, silicone and the like.

Turning now to FIGS. 5-9, an over shoe in accordance with another embodiment of the present disclosure is shown generally as 10a. Over shoe 10a is substantially similar to over shoe 10 and will be discussed in detail to the extent necessary to identify differences in construction and operation. As seen in FIGS. 5-9 bottom wall 18 includes a longitudinally oriented slot 30 extending substantially the entire length of over shoe 10a. Accordingly, slot 30 enables over shoe 10a to be slipped over and onto, for example, jaw members 280, 282, having widths which are larger than the width of tissue contacting wall 12 and/or larger than the width of opening 22 formed at the proximal end thereof. In other words, as seen in FIGS. 8 and 9, slot 30 enables and/or allows side walls 14, 16 to deflect and/or bow orthogonally outward (as indicated by arrows "A") when a jaw member 280, 282 is inserted into over shoe 10a.

Figure 10:
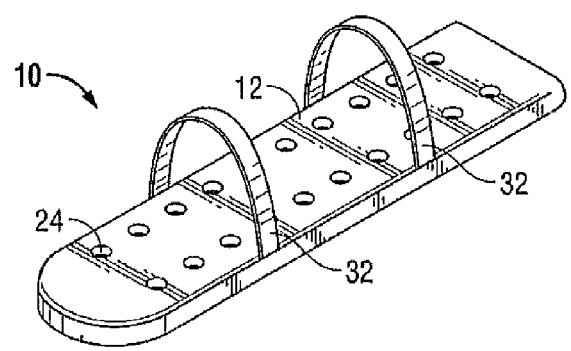
FIG. 10 is a bottom perspective view of an over shoe in accordance with still another embodiment of the present disclosure.

Tuning now to FIG. 10, an over shoe, in accordance with yet another embodiment of the present disclosure, is shown generally as 10b. Over shoe 10b is substantially similar to over shoe 10 and will only be discussed in detail to the extent necessary to identify differences in construction and operation. As seen in FIG. 10, over shoe 10b includes at least one, preferably a pair of bands 32 secured to and extending across tissue contacting wall 12. Preferably, bands 32 are elastic and enable over shoe 10b to be slipped onto and/or into engagement with jaw members 280, 282 of varying width and/or thickness. While elastic bands 32 are preferred, it is envisioned and within the scope of the present disclosure for bands 32 to be inelastic, capable of being tied to one another and/or capable of being releasably secured to one another (e.g., hook and loop type fasteners).

Figure 11:
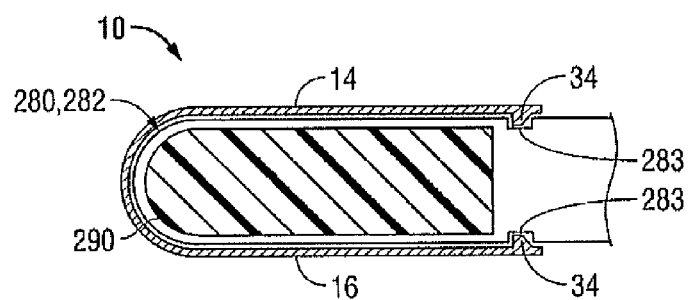
FIG. 11 is a top plan view of a jaw member of a forceps including an over shoe, with the tissue contacting wall thereof removed therefrom, mounted thereon and illustrating an exemplary positioning arrangement for engagement of the over shoe to the jaw member.

Turning now to FIG. 11, an exemplary positioning arrangement for the engagement of over shoe 10 to a jaw member 280, 282 of forceps 100 or 200, is shown. As seen in FIG. 11, the inner surface of one, preferably each side wall 14, 16 of over shoe 10 includes a nub, projection or the like 34 extending therefrom. Nubs 34 preferably engage with and/or are received in corresponding recesses 283 formed in the side surfaces of jaw members 280, 282, in a snap-fit type engagement. In this manner, when over shoe 10 is slipped onto and/or over one of jaw members 280, 282 of forceps 100 or 200, the positioning arrangement fixes the location and/or position of the apertures (not shown) on jaw member 280 or 282. Meanwhile, when over shoe 10 is slipped onto and/or over the other of jaw members 280, 282 of forceps 100 or 200, the positioning arrangement fixes the location and/or position of the apertures (not shown) on the other of jaw member 280 or 282. In this manner, the position of the apertures (not shown) on jaw member 280 can be fixed and predetermined relative to the position of the apertures (not shown) on jaw member 282. For example, apertures 24 of over shoe 10 corresponding to jaw member 280 can be in juxtaposed vertical registration or in juxtaposed offset registration with apertures 24 of over shoe 10 corresponding to jaw member 282 depending on a particular purpose.

As best seen in FIG. 11, various electrical connections of electrode assemblies 110, 210 (not shown) are configured to provide electrical continuity to a series of electrode pads 290 disposed atop at least one of jaw members 280, 282 for transmitting electrosurgical energy to the tissue. When the over shoe 10 is electrically conductive, different electrical connections would obviously apply.

Figure 12:
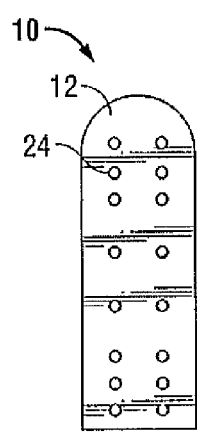
FIG. 12 is a top plan view of an over shoe illustrating an exemplary aperture pattern formed therein.

Turning now to FIGS. 12-15, exemplary illustrations of various arrangements and patterns of apertures 24, formed in tissue contacting wall 12, are shown for use with either an electrically conductive overshoe or an electrically insulative over shoe. As seen in FIG. 12, apertures 24 are unevenly distributed and/or formed in tissue contacting wall 12. In particular, there is shown an increased density of apertures 24 formed in both a distal region and a proximal region of tissue contacting wall 12 and a reduced density of apertures 24 formed in a central region of tissue contacting wall 12.

Figure 13:
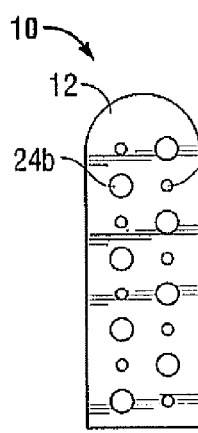
FIG. 13 is a top plan view of an over shoe illustrating another exemplary aperture pattern formed therein.

As seen in FIG. 13, tissue contacting wall 12 of over shoe 10 can be provided with at least two longitudinally oriented rows of alternatingly-sized apertures, namely, relatively larger sized apertures 24a and relatively smaller sized apertures 24b.

Figure 14:
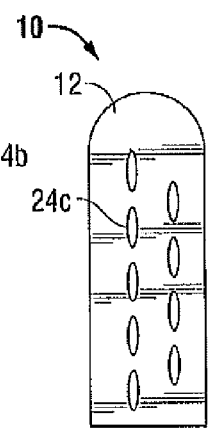
FIG. 14 is a top plan view of an over shoe illustrating still another exemplary aperture pattern formed therein.
Figure 15:
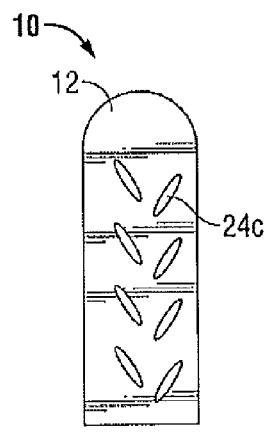
FIG. 15 is a top plan view of an over shoe illustrating yet another exemplary hole pattern formed therein.

As seen in FIG. 14, tissue contacting wall 12 of over shoe 10 can be provided with at least two longitudinally-oriented, preferably offset, rows of elongate slots 24c formed therein. As seen in FIG. 15, slots 24c can be oriented at an angle with respect to a longitudinal axis of tissue contacting wall 12.

While FIGS. 12-15 illustrate exemplary arrangements and/or patterns of apertures that can be formed in tissue contacting wall 12 of over shoe 10, in no way is this to be an exhaustive illustration of all of the arrangements and/or patterns that can be formed in tissue contacting wall 12. For example, any of the arrangements and/or patterns illustrated in FIGS. 12-15 can be interchanged and/or combined with one another in any order, orientation and/or density.

Figure 16:
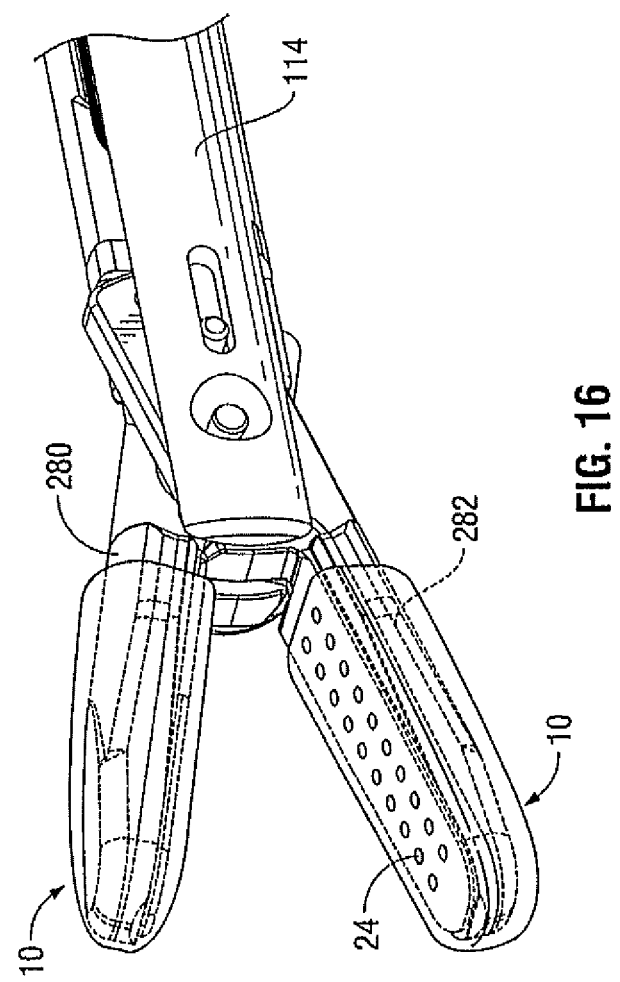
FIG. 16 is an enlarged perspective view of the jaw assembly of the endoscopic forceps of FIG. 1A, illustrating the placement of an over shoe, in accordance with the present disclosure, thereon.
Figure 17:
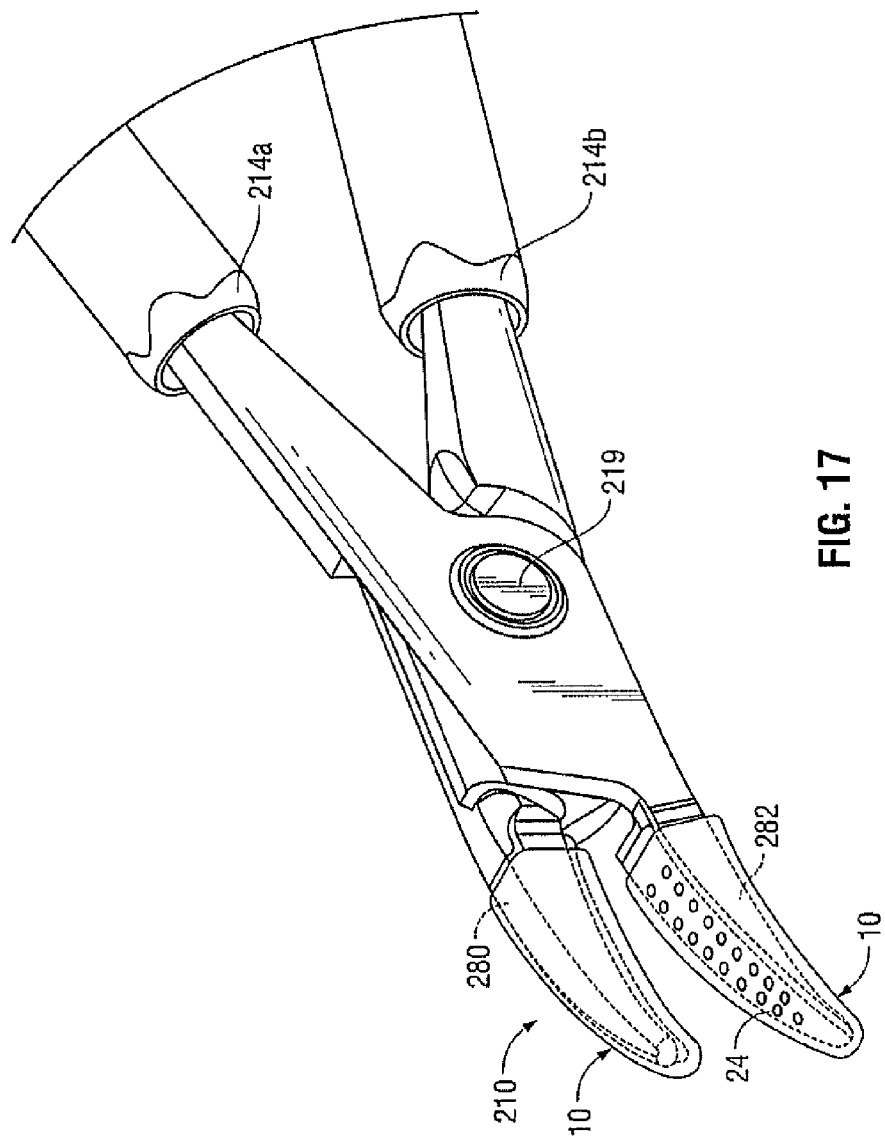
FIG. 17 is an enlarged perspective view of the jaw assembly of the endoscopic forceps of FIG. 2A, illustrating the placement of an over shoe, in accordance with the present disclosure, thereon.

As seen in FIG. 16, over shoes 10, configured and dimensioned to be slipped over jaw members 280, 282 of forceps 100, are shown in position over each jaw member 280, 282 thereof. As seen in FIG. 17, over shoes 10, configured and dimensioned to be slipped over jaw members 280, 282 of forceps 200, are shown in position over each jaw member 280, 282 thereof.

Although the majority of the figure drawings depict an over shoe for use with a bipolar forceps for use in connection with endoscopic surgical procedures, over shoes for open forceps are also contemplated for use in connection with traditional open surgical procedures.

In use, as depicted in the insulating embodiment of FIGS. 18A-18D, over shoe 10 positioned on at least one of jaw members 280, 282, the surgeon initially approximates tissue "T" (see FIG. 18A) between the opposing jaw members 280, 282 and then grasps tissue "T" (see FIG. 18B) by manipulating forceps 100 or 200 to approximate jaw members 280, 282 towards one another. Once tissue "T" is grasped, the surgeon selectively activates electrosurgical generator (see FIG. 18C) to supply electrosurgical energy to electrode pad 290 of each jaw member 280, 282. In particular, electrosurgical energy flows from the positive terminal of electrosurgical generator, to electrode pad 290 of jaw member 282, through aperture 24 of over shoe 10 placed on jaw member 282, through tissue "T", through aperture 24 of over shoe 10 placed on jaw member 280, to electrode pad 290 of jaw member 280, and back to the negative terminal of electrosurgical generator. As a result thereof, an intermittent pattern of tissue seals and/or welds "W" are created along tissue "T" (see FIGS. 18C and 18D).

The arrangement and/or pattern of apertures 24 formed in over shoes 10 only permits the sealing and/or welding of tissue "T" which is located between juxtaposed apertures 24 of over shoes 10 placed on each jaw member 280, 282. Tissue "T" adjacent each aperture 24 remains viable which, as can be appreciated, allows blood and nutrients to flow through the sealed tissue "T" and between the individual tissue welds "W" as indicated by arrows "F" of FIG. 18D, to promote tissue healing and reduce the chances of tissue necrosis. As mentioned above, a conductive over shoe 10 may be used to obtain a similar surgical result.

A controller "C" (see FIG. 18C) may be electrically interposed between electrosurgical generator and electrode pads 290 to regulate the electrosurgical energy supplied thereto depending upon certain electrical parameters, such as, for example, current impedance, temperature, voltage, tissue type, tissue thickness, etc. For example, the forceps or controller "C" may include one or more sensors and/or smart sensors (not shown) which communicate with electrosurgical generator (or with a smart circuit, a computer, a feedback loop, etc.) to automatically regulate the electrosurgical intensity (e.g., waveform, current, voltage, etc.) to enhance the sealing and/or welding process. The sensors may measure or monitor one or more of the following parameters: tissue temperature, tissue impedance at the weld site, the change in impedance of the tissue over time and/or changes in power or current applied in the tissue over time. An audible or visual feedback monitor (not shown) may be employed to convey to the surgeon regarding the overall seal quality of the completion of an effective tissue seal.

Moreover, a PCB (printed circuit board) circuit or flex circuit (not shown) may be utilized to provide information relating to the gap distance (e.g., with a proximity detector) between jaw members 280, 282, the sealing pressure between jaw members 280, 282 prior to and during activation, load (e.g., with a strain gauge), the thickness of tissue "T" prior to or during activation, the impedance across the tissue during activation, and the rate of tissue expansion during activation and sealing.

Several examples of such devices and systems are described in commonly-owned U.S. application Ser. No. 10/427,832 the entire contents of which are hereby incorporated by reference herein. Methods and systems for adjusting and setting the gap distance are also disclosed in commonly assigned U.S. Provisional Patent Application Ser. No. 60/470, 632, the entire contents also being hereby incorporated by reference herein. Methods and systems for controlling the output of RF medical generators are disclosed in commonly assigned U.S. patent application Ser. No. 10/417,823, the entire contents being hereby incorporated by reference herein.

It is envisioned that the PCB circuit may be designed to provide electrical feedback to electrosurgical generator relating to one or more of the above parameters either on a continuous basis or upon inquiry from electrosurgical generator. For example, a PCB circuit may be employed to control the power, current and/or type of current waveform delivered from electrosurgical generator to jaw members 280, 282 in order to reduce collateral damage to surrounding tissue during activation, e.g., thermal spread, tissue vaporization and/or steam from the treatment site. Examples of various control circuits, generators and algorithms which may be utilized are disclosed in U.S. Pat. No. 6,228,080 and U.S. patent application Ser. No. 10/073,761, the entire contents of both of which are hereby incorporated by reference herein.

From the foregoing and with reference to the various figure drawings, those skilled in the art will appreciate that certain modifications can also be made to the present disclosure without departing from the scope of the same. For example, it is envisioned that the diameter of the apertures of the over shoe may be varied during the manufacturing process of the over shoe according to the type of surgical instrument to be used. In particular, it is envisioned that one sized aperture diameter may be used for electrosurgical blades for coagulating or cutting tissue while another aperture diameter may be used for electrosurgical forceps which utilize a combination of closing force, gap distance between jaw members and amount of electrosurgical energy, to seal tissue.

Moreover, it is envisioned that the number of apertures per square inch (or per square centimeter) may be modified during the manufacturing process to control the treatment area and minimize the collateral effect to surrounding tissue. In addition, as discussed above, the shape of the apertures include and are not limited to circular, triangular, rectangular, oval and the like. It is also contemplated that the thickness of the tissue contacting wall 12 of the over shoe 10 may be modified during the manufacturing process to establish a preferred resistance and voltage for creating a desired surgical effect.

Figure 19A:
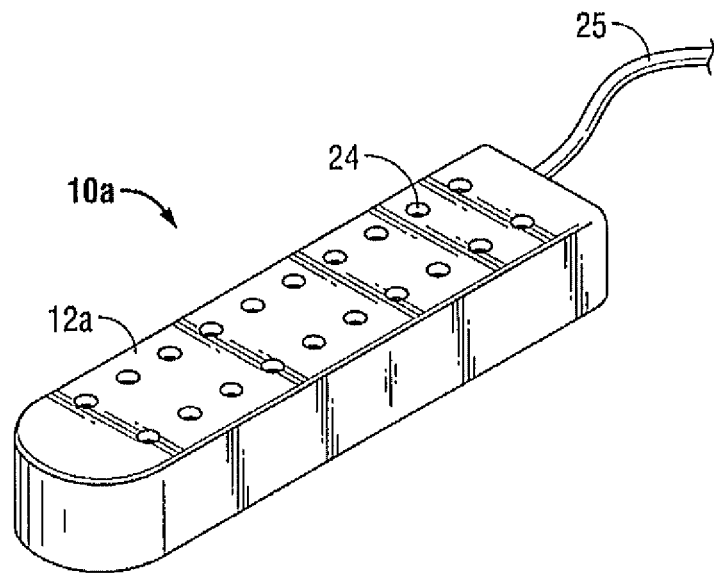
FIG. 19A is a schematic, perspective view of an alternate embodiment of the present disclosure showing a conductive over shoe.

As mentioned repeatedly above, it is further envisioned that the jaw members 280, 282 of forceps 100 can be insulative and that an over shoe 10, or preferably, tissue contacting wall 12 of over shoe 10, is fabricated from a conductive material and electrically connected to an electrosurgical energy source (See FIG. 19A). In this manner, any non-electrosurgical forceps can be retrofitted with over shoe 10 placed on or slipped over at least one of its jaw members. Apertures 24 of over shoe 10 in turn act as cooling spots (i.e., regions where limited electrosurgical energy or thermal energy is transmitted). In this manner, following use and application of electrosurgical energy to tissue "T", the regions where over shoe 10 contacts tissue "T" is where tissue sealing and/or welding occurs and the regions where apertures 24 are located do not experience tissue sealing and/or welding and remain viable tissue. As can be appreciated, each over shoe would be attachable to a different electrical potential emanating from an electrosurgical generator such that the over shoes are capable of conducting bipolar electrosurgical energy through tissue held therebetween. As such, wires or conductive elements 25 would be used to accomplish this purpose.

Figure 19B:
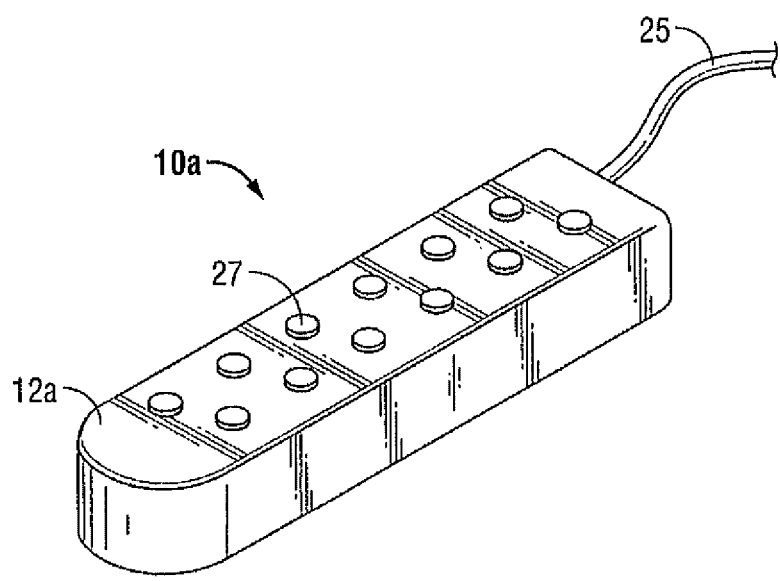
FIG. 19B is a schematic, perspective view of another alternate embodiment of the present disclosure showing a conductive over shoe with raised conductive projections.

As best seen in FIG. 19B, it is also contemplated that over shoe 10 can include electrically conductive tissue contacting portions 27 or projections in lieu of apertures 24. For example, tissue contacting wall 12a and/or electrically conductive tissue contacting portions 27 may be arranged on surface 12a to project therefrom to create a pattern of tissue welds for treating tissue. It is also envisioned that the projections 27 can be coated with non-stick materials. When utilized on these surfaces, the non-stick materials provide an optimal surface energy for eliminating sticking due in part to the surface texture and the susceptibility to surface breakdown due to electrical effects and corrosion in the presence of biologic tissues. As can be appreciated, reducing the amount that the tissue "sticks" during sealing improves the overall efficacy of the instrument.

The non-stick materials may be manufactured from one (or a combination of one or more) of the following "non-sticks" materials, namely, nickel-chrome, chromium nitride, Med-Coat 2000 manufactured by The Electrolizing Corporation of OHIO, Inconel 600 and tin-nickel. Inconel 600 is a so-called "super alloy" which is manufactured by Special Metals, Inc. located in Conroe Tex. Super alloys are primarily used in environments which require resistance to corrosion and heat. The high Nickel content of Inconel 600 makes the material especially resistant to organic corrosion. As can be appreciated, these properties are desirable for bipolar electrosurgical instruments which are naturally exposed to high temperatures, high RF energy and organic matter.

One particular class of materials disclosed herein has demonstrated superior non-stick properties and, in some instances, superior micro-seal quality. For example, nitride coatings which include, but not are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reduce overall sticking. For example, high nickel/chrome alloys with a Ni/Cr ratio of approximately 5:1 have been found to significantly reduce sticking in bipolar instrumentation.

While the above disclosure and figures relate to hemostats, forceps or bipolar instruments, it is contemplated and within the scope of the present disclosure that the over shoes disclosed herein can be used in connection with and/or association with electrosurgical pencils and the like.

Although the present disclosure has been described with respect to particular embodiments, it will be readily apparent to those having ordinary skill in the art to which it pertains, that changes and modifications may be made thereto without departing from the spirit or scope of the disclosure.

What is claimed is:

1. An over shoe selectively positionable on at least one jaw member of an electrosurgical instrument having two opposing jaw members, the over shoe comprising:
   a substantially planar tissue contacting wall configured to overlay a tissue contacting surface of the at least one jaw member and having a plurality of apertures defined therein;
   a side wall having a first edge and a second edge, wherein the first edge is joined to a perimetric edge of the tissue contacting wall; and
   a bottom wall joined along an edge thereof to the second edge of the side wall;
   wherein inner surfaces of the tissue contacting wall, the side wall, and the bottom wall are configured to frictionally retain the over shoe on the at least one jaw member of the electrosurgical instrument.

2. The over shoe according to claim 1, wherein the apertures are evenly sized.

3. The over shoe according to claim 1, wherein the apertures are circular.

4. The over shoe according to claim 3, wherein the apertures have a diameter of between 10 μm and 1000 μm.

5. The over shoe according to claim 1, wherein the apertures are elongated slots.

6. The over shoe according to claim 5, wherein the elongated slots are in a parallel orientation with respect to each other.

7. The over shoe according to claim 1, wherein the tissue contacting wall includes a plurality of apertures arranged in pairs along its length.

8. The over shoe in according to claim 1, further comprising a longitudinally oriented slot defined in the bottom wall and extending along at least a portion of the length of the bottom member.

9. The over shoe according to claim 1, wherein the tissue contacting wall is formed from an insulative material.

10. The over shoe according to claim 1, wherein the tissue contacting wall is formed from conductive material.

11. An over shoe selectively positionable on at least one jaw member of an electrosurgical instrument having two opposing jaw members, the over shoe comprising:
    a substantially planar tissue contacting wall formed from a non-conductive material and being configured to overlay an electrode of a first jaw member of the two opposing jaw members;
    a side wall having a first edge and a second edge, wherein the first edge is joined to a perimetric edge of the tissue contacting wall;
    a bottom wall joined along an edge thereof to the second edge of the side wall;
    wherein inner surfaces of the tissue contacting wall, the side wall, and the bottom wall are configured to frictionally retain the over shoe on the at least one jaw member of the electrosurgical instrument; and
    a protrusion extending from the tissue contacting wall and configured to electrically communicate with an electrode of the first jaw member when the overshoe is selectively positioned on the first jaw member.

12. The over shoe according to claim 11, wherein the protrusion is configured to create a pattern of tissue welds for treating tissue.

13. The over shoe according to claim 11, wherein the protrusion is coated with non-stick material, wherein the non-stick material is selected from the group consisting of nickel-chrome, chromium nitride and tin-nickel.

14. An over shoe selectively positionable on at least one jaw member of an electrosurgical instrument, the over shoe comprising:
   a non-conductive material configured to overlay a tissue-contacting surface of at least one jaw member of the electrosurgical instrument, the non-conductive material having a tissue-contacting wall and an inner surface, the non-conductive material including a plurality of apertures extending between the tissue-contacting wall and the inner surface;
   wherein the inner surface of the tissue-contacting wall is configured to frictionally retain the over shoe on the at least one jaw member of the electrosurgical instrument.

* * * * *